(12) United States Patent
Van Egmond et al.

(10) Patent No.: US 7,074,979 B2
(45) Date of Patent: Jul. 11, 2006

(54) PROCESSING A CONTAMINATED OXYGENATE-CONTAINING FEED STREAM IN AN OXYGENATE TO OLEFIN REACTION SYSTEM

(75) Inventors: Cor F. Van Egmond, Pasadena, TX (US); Michael Peter Nicoletti, Houston, TX (US); Ronald G. Searle, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 350 days.

(21) Appl. No.: 10/421,012

(22) Filed: Apr. 22, 2003

(65) Prior Publication Data

US 2004/0127763 A1 Jul. 1, 2004

Related U.S. Application Data

(60) Provisional application No. 60/437,698, filed on Dec. 31, 2002.

(51) Int. Cl.
*C07C 1/00* (2006.01)
(52) U.S. Cl. ...................... 585/640; 585/639
(58) Field of Classification Search .............. 585/639, 585/640
See application file for complete search history.

(56) References Cited

U.S. PATENT DOCUMENTS 2,877,747 A 3/1959 Happell ...................... 122/435

(Continued)

FOREIGN PATENT DOCUMENTS

WO   WO 02/00579    1/2002

OTHER PUBLICATIONS

Yang et al., "Physical and Chemical Properties and Handling Aspect", Chapter 2, pp. 554, Northwestern University, Evanston, Illinois (1994).

(Continued)

*Primary Examiner*—Walter D. Griffin
*Assistant Examiner*—In Suk Bullock

(57) ABSTRACT

A feed vaporization process and apparatus for oxygenate to olefin conversion is provided, which uses a vapor-liquid disengaging drum to separate non-volatiles and/or low-volatiles from volatiles in the oxygenate feed and produce a vaporized effluent that is reduced in non-volatiles and/or low-volatiles while at the same time maintaining the effluent at optimal temperature and pressure as a feed for oxygenate to olefin conversion. The feed vaporization process and apparatus is particularly well suited for selectively removing non-volatile contaminants such as soot and rust from an oxygenate-containing feed, which may have become contaminated during shipping.

50 Claims, 2 Drawing Sheets

U.S. PATENT DOCUMENTS

| | | | |
|---|---|---|---|
| 4,083,888 A | 4/1978 | Caesar et al. | 200/682 |
| 4,098,412 A | 7/1978 | Shakshober | 214/15 D |
| 4,163,455 A | 8/1979 | Hebert et al. | 134/167 R |
| 4,433,189 A | 2/1984 | Young | 585/640 |
| 4,665,249 A | 5/1987 | Mao et al. | 585/408 |
| 4,777,321 A | 10/1988 | Harandi et al. | 585/640 |
| 4,814,535 A | 3/1989 | Yurchak | 585/408 |
| 4,814,536 A | 3/1989 | Yurchak | 585/408 |
| 4,826,662 A | 5/1989 | Mao et al. | 422/190 |
| 5,028,400 A | 7/1991 | Harandi et al. | 422/211 |
| 5,059,738 A | 10/1991 | Beech, Jr. et al. | 585/469 |
| 5,189,975 A | 3/1993 | Zednik et al. | 114/74 |
| 5,335,615 A | 8/1994 | Bjorkman | 114/74 R |
| 5,398,629 A | 3/1995 | Wasenius | 114/74 R |
| 5,638,845 A | 6/1997 | Oliver et al. | 134/167 R |
| 5,714,662 A * | 2/1998 | Vora et al. | 585/640 |
| 5,899,162 A | 5/1999 | Beaupreet et al. | 114/74 A |
| 6,021,848 A | 2/2000 | Breivik et al. | 166/344 |
| 6,041,726 A | 3/2000 | Filek | 114/74 R |
| 6,121,504 A | 9/2000 | Kuechler et al. | 585/640 |
| 6,166,282 A | 12/2000 | Miller | 585/638 |
| 6,846,966 B1 * | 1/2005 | Lumgair et al. | 585/639 |
| 6,899,046 B1 * | 5/2005 | Searle et al. | 114/74 R |

OTHER PUBLICATIONS

U.S. Appl. No 10/020,732 filed Oct. 30, 2001, Lumgair et al.

* cited by examiner

PROCESSING A CONTAMINATED OXYGENATE-CONTAINING FEED STREAM IN AN OXYGENATE TO OLEFIN REACTION SYSTEM

CROSS REFERENCE TO RELATED APPLICATIONS

The present application claims the benefit of U.S. Provisional Application No. 60/437,698 filed Dec. 31, 2002, the entire content of which is incorporated herein by reference.

FIELD OF THE INVENTION

The present invention relates to processing an oxygenate-containing feed stream, and more particularly, to selectively removing contaminants from an oxygenate-containing feed stream for an oxygenate to olefin reaction system.

BACKGROUND OF THE INVENTION

Light olefins such as ethylene, propylene and mixtures thereof, serve as feeds for the production of numerous important chemicals and polymers. Typically, light olefins are produced by cracking petroleum feeds. Because of the limited supply of competitive petroleum feeds, the opportunities to produce low cost light olefins from petroleum feeds are limited. Efforts to develop light olefin production technologies based on alternative feeds have increased.

Oxygenates, such as, for example, alcohols, particularly methanol, ethanol, n-propanol, and iso-propanol, dimethyl ether, methyl ethyl ether, diethyl ether, dimethyl carbonate, and methyl formate are an important type of alternate feed for the production of light olefins. Many of these oxygenates may be produced by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates have promise as an economical, non-petroleum source for light olefin production.

The petrochemical industry has known for some time that oxygenates, especially alcohols, are convertible into light olefins. For example, methanol, the preferred alcohol for light olefin production, may be converted to primarily ethylene and propylene in the presence of a molecular sieve catalyst. Oxygenate-containing feeds, particularly inexpensive oxygenate-containing feeds, may contain impurities which are deleterious to the catalysts employed in oxygenate to olefin conversion processes. Such impurities include low-volatile materials and non-volatile materials that have negligible vapor pressure at the conditions necessary to prepare feed for the oxygenates to olefin conversion process.

Although low-volatile and non-volatile materials are not normally found in freshly produced oxygenated hydrocarbons, they can be introduced during storage and handling of oxygenates, as well as during recycling of oxygenate streams to a reactor. Because of catalyst sensitivity in an oxygenates to olefins conversion reactor, even small amounts of non-volatile and/or low-volatile contaminants such as metals, salts and heavy hydrocarbons in the feed can accumulate on and thus poison the reactor's catalyst. These poisons interfere with the catalyst's function, reducing the life and selectivity of the catalyst, which results in increased overall production costs. Given that non-volatiles in the feed at levels as low as one wppm can accumulate to 12,000 wppm on the catalyst inventory, a compelling interest exists to provide feeds of extremely reduced non-volatiles content. Other processes have been taught that attempt to reduce the amount of catalyst poisons in the OTO reactor feed.

U.S. patent application Ser. No. 10/020,732, filed Oct. 30, 2001, entitled "Heat Recovery in an Olefin Production Process," the entirety of which is incorporated herein by reference, discloses a process for removing heat from an effluent stream while maintaining a temperature of the gas phase above the dew point. By following this process, some solid particles and some other contaminants may be separated from the oxygenates. By removing these contaminants, the catalysts in the OTO reactor will perform better and last longer, thereby improving the reactor's efficiency and reducing production costs. Unfortunately, this process does not remove all catalyst poisons and further creates difficulties in maintaining the effluent at a proper temperature and pressure.

It should thus be appreciated that a delicate balance exists between providing an inexpensive contaminated oxygenate-containing feed for an OTO reactor while ensuring that the contaminants in the oxygenate-containing feed do not significantly poison an OTO reactor catalyst. That is, it is desirable to maximize the amount of contaminants in a feed stream in order to obtain low oxygenate purification costs, while maintaining a low enough level of poisoning contaminants that OTO reaction efficiency is not significantly reduced. Accordingly, it would be desirable to provide a process that effects substantial removal of poisoning contaminants, while at the same time allowing non-poisoning contaminants to enter the OTO reaction system.

SUMMARY OF THE INVENTION

The present invention provides a feed vaporization and introduction (FVI) system which selectively separates non-volatile and/or low-volatile contaminants in an oxygenate-containing feed from volatile contaminants contained therein. The FVI system separates the oxygenate-containing feed into a vaporized feed stream, which contains vaporized oxygenates such as methanol and volatile contaminants, and a substantially liquid stream, which contains non-volatile contaminants such as soot and rust and/or low-volatile contaminants such as heavy hydrocarbons. The vaporized oxygenate-containing feed is directed to an oxygenate-to-olefin (OTO) reaction system for conversion to light olefins. Preferably, the OTO reaction system is a methanol-to-olefin (MTO) reaction system. The FVI system advantageously provides the ability to direct an inexpensive contaminated oxygenate-containing feed, e.g., a methanol-containing stream that does not pass specification for grade A or AA methanol, to an OTO reaction system.

In one embodiment, the invention provides a process for converting methanol to light olefins. The process includes the step of providing a feedstock comprising methanol and a contaminant selected from the group consisting of: soot, rust, $SO_x$, carbonic acid, and $C_5$-hydrocarbons. The feedstock does not pass specification for Grade A methanol. The methanol contacts a catalyst in a reactor under conditions effective to convert at least a portion of the methanol to light olefins.

In another embodiment, the inventive process includes the step of providing a feedstock comprising liquid methanol and a contaminant selected from the group consisting of $SO_x$, carbonic acid, and $C_5$-hydrocarbons. At least a portion of the feedstock is vaporized to form a vaporized feed stream, wherein the vaporized feed stream comprises vaporized methanol and at least a portion of the contaminant that was present in the feedstock. The vaporized methanol contacts a catalyst in a reactor under conditions effective to convert at least a portion of the vaporized methanol to light olefins.

In one embodiment, the inventive process includes the step of providing a feedstock comprising liquid methanol and a contaminant selected from the group consisting of soot and rust. At least a portion of the feedstock is vaporized to form a vaporized feed stream and a blowdown stream, wherein the vaporized feed stream comprises vaporized methanol, and wherein the blowdown stream comprises at least a portion of the contaminant that was present in the feedstock. The vaporized methanol contacts a catalyst in a reactor under conditions effective to convert at least a portion of the vaporized methanol to light olefins.

In another embodiment, the inventive process includes the step of providing a methanol-containing stream comprising liquid methanol and solid contaminants, wherein the methanol-containing stream does not pass specification for Grade A methanol. The methanol-containing stream is subjected to conditions, e.g., temperature and pressure, effective to form a vaporized feed stream and a liquid blowdown stream, wherein the vaporized feed stream comprises vaporized methanol, and the liquid blowdown stream comprises the solid contaminants and optionally low-volatile contaminants. The vaporized methanol contacts a catalyst under conditions effective to convert at least a portion of the vaporized methanol to light olefins.

BRIEF DESCRIPTION OF THE DRAWINGS

This invention will be better understood by reference to the Detailed Description of the Invention when taken together with the attached drawings, wherein.

DETAILED DESCRIPTION OF THE INVENTION

A. Introduction

Figure 1:
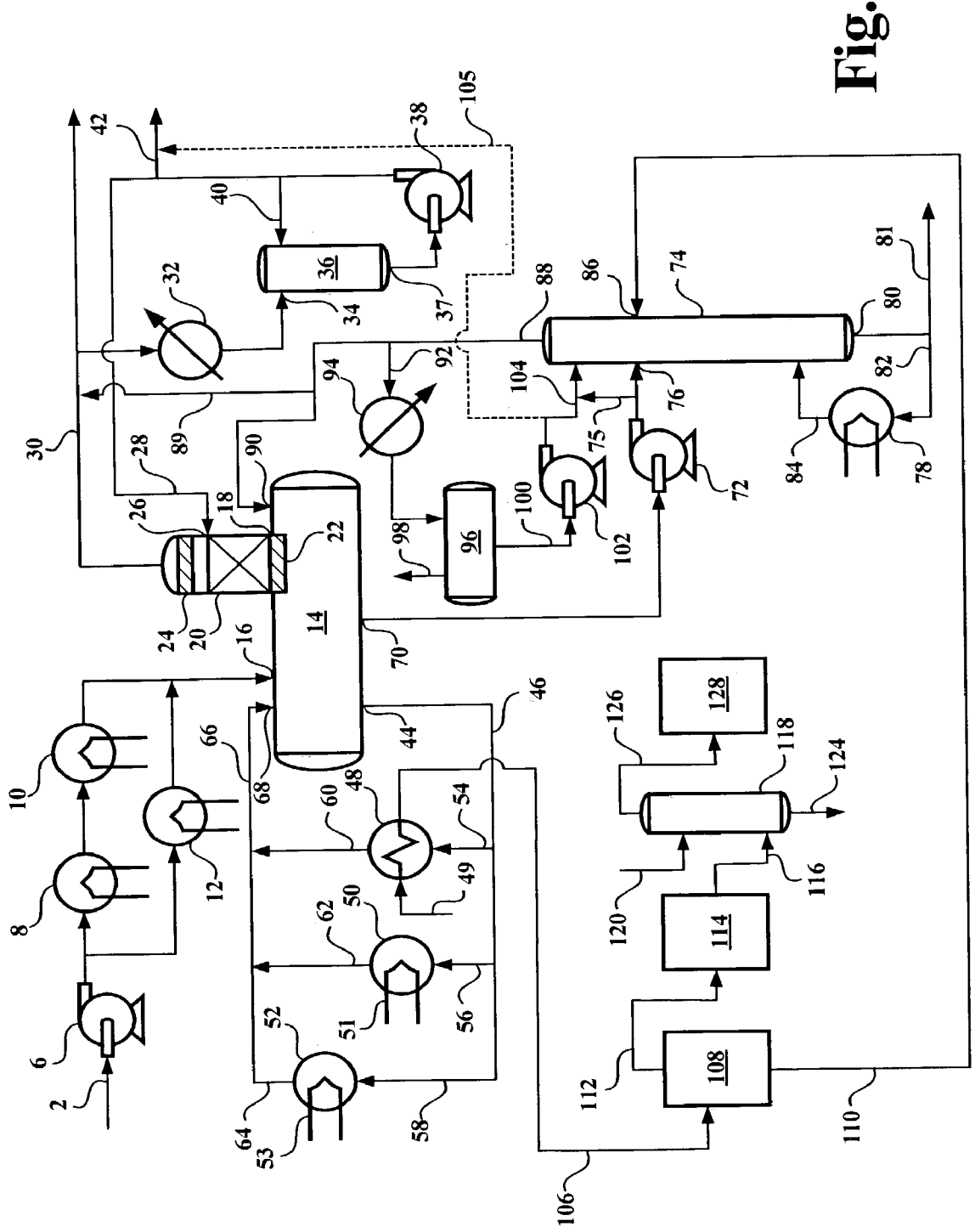
FIG. 1 depicts a schematic of one embodiment of the present invention.

The present invention provides a feed vaporization and introduction (FVI) system which selectively separates non-volatile and/or low-volatile contaminants in an oxygenate-containing feed from volatile contaminants contained therein. The FVI system separates the oxygenate-containing feed into a vaporized feed stream, which contains vaporized oxygenates such as methanol and volatile contaminants, and a substantially liquid stream, which contains non-volatile contaminants such as soot and rust and/or low-volatile contaminants such as heavy hydrocarbons. The vaporized oxygenate-containing feed is directed to an oxygenate-to-olefin (OTO) reaction system for conversion to light olefins. Preferably, the OTO reaction system is methanol-to-olefin (MTO) reaction system. The FVI system advantageously provides the ability to direct an inexpensive contaminated oxygenate-containing feed, e.g., a methanol-containing stream that does not pass specification for grade A or AA methanol, to an OTO reaction system.

B. The Oxygenate to Olefin Reaction Process

The present invention relates to an OTO reaction system or process. The most preferred OTO process is generally referred to as a gas-to-olefins (GTO) or alternatively an MTO reaction process. In an MTO reaction process, methanol in a methanol-containing feedstock is converted in the presence of a molecular sieve catalyst composition into one or more olefins, preferably and predominantly, ethylene and/or propylene, often referred to as light olefins.

The preferred MTO process and reaction conditions will now be described in more detail. Preferably, the conditions in the MTO reactor including the pressure, temperature, weight hourly space velocity (WHSV), etc., are conducive to converting the methanol to light olefins, as discussed below. Typically, molecular sieve catalysts are used to convert oxygenate compounds to light olefins. Silicoaluminophosphate (SAPO) molecular sieve catalysts are particularly desirable in such conversion processes, because they are highly selective in the formation of ethylene and propylene.

The feedstock preferably contains one or more aliphatic-containing compounds that include alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from about 1 to about 50 carbon atoms, preferably from about about 1 to about 20 carbon atoms, more preferably from about 1 to about 10 carbon atoms, and most preferably from about 1 to about 4 carbon atoms.

Non-limiting examples of aliphatic-containing compounds include alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as dimethyl ether, diethyl ether and methylethyl ether, alkyl-halides such as methyl chloride and ethyl chloride, alkyl ketones such as dimethyl ketone, formaldehydes, and various acids such as acetic acid.

In a preferred embodiment of the process of the invention, the feedstock contains one or more oxygenates, more specifically, one or more organic compounds containing at least one oxygen atom. In the most preferred embodiment of the process of the invention, the oxygenate in the feedstock is one or more alcohols, preferably aliphatic alcohols where the aliphatic moiety of the alcohols has from about 1 to about 20 carbon atoms, preferably from about 1 to about 10 carbon atoms, and most preferably from about 1 to about 4 carbon atoms. The alcohols useful as feedstocks in the process of the invention include lower straight and branched chain aliphatic alcohols and their unsaturated counterparts. Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, are converted primarily into one or more olefins. The olefins or olefin monomer(s) produced from the feedstock typically have from about 2 to about 30 carbon atoms, preferably from about 2 to about 8 carbon atoms, more preferably from about 2 to about 6 carbon atoms, still more preferably from about 2 to about 4 carbons atoms, and most preferably ethylene and/or propylene.

Non-limiting examples of olefin monomers include ethylene, propylene, butene-1, pentene-1, 4-methyl-pentene-1, hexene-1, octene-1 and decene-1, preferably ethylene, propylene, butene-1, pentene-1, 4-methyl-pentene-1, hexene-1, octene-1 and isomers thereof. Other olefin monomers include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition into one or more olefins having from about 2 to about 6 carbons atoms, preferably from about 2 to about 4 carbon atoms. Most preferably, the olefins, alone or in combination, are converted from a feedstock containing an oxygenate, preferably an alcohol, most preferably methanol, to the preferred olefins ethylene and/or propylene.

The feedstock, in one embodiment, contains one or more diluents, typically used to reduce the concentration of the feedstock. The diluents are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. In other embodiments, the feedstock does not contain any diluent.

The diluent may be used either in a liquid or a vapor form, or a combination thereof. The diluent is either added directly to the feedstock entering into the reactor or added directly into the reactor, or added with the molecular sieve catalyst composition. In one embodiment, the amount of diluent in the feedstock is in the range of from about 1 to about 99 mole percent based on the total number of moles of the feedstock and diluent, preferably from about 1 to about 80 mole percent, more preferably from about 5 to about 50, most preferably from about 5 to about 25. In one embodiment, other hydrocarbons are added to the feedstock either directly or indirectly, and may include olefin(s), paraffin(s), aromatic(s) (see for example U.S. Pat. No. 4,677,242) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (optionally a turbulent bed process), preferably a continuous fluidized bed process, and most preferably a continuous high velocity fluidized bed process.

The reaction processes may take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described, for example, in U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference. Dual riser reactors or other reactor designs optionally include a plurality of feed introduction nozzles.

The preferred reactor type is a riser reactor generally described in *Riser Reactor, Fluidization and Fluid-Particle Systems*, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613, filed May 4, 2000 (multiple riser reactor), which are all herein fully incorporated by reference.

In one embodiment, the amount of fresh feedstock fed separately or jointly with a vapor feedstock to a reactor system is in the range of from about 0.1 weight percent to about 95 weight percent, preferably from about 10 weight percent to about 90 weight percent, more preferably from about 50 weight percent to about 85 weight percent, based on the total weight of the feedstock including oxygenate recycle and any diluent contained therein. The liquid and vapor feedstocks are preferably the same composition, or contain varying proportions of the same or different feedstock with the same or different diluent.

The conversion temperature employed in the conversion process, specifically within the reactor system, is in the range of from about 200° C. (392° F.) to about 1000° C. (1832° F.), preferably from about 250° C. (392° F.) to about 800° C. (1472° F.), more preferably from about 250° C. (482° F.) to about 750° C. (1382° F.), yet more preferably from about 300° C. (572° F.) to about 650° C. (1202° F.), yet even more preferably from about 350° C. (662° F.) to about 600° C. (1112° F.), and most preferably from about 350° C. (662° F.) to about 550° C. (1022° F.).

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa (0.015 psia) to about 5 MPaa (730 psia), preferably from about 5 kPaa (0.73 psia) to about 1 MPaa (145 psia), and most preferably from about 20 kPaa (2.9 psia) to about 500 kPaa (72.5 psia).

The weight hourly space velocity (WHSV), particularly in a process for converting a feedstock containing one or more oxygenates in the presence of a molecular sieve catalyst composition within a reaction zone, is defined as the total weight of the feedstock, excluding any diluents, that is fed to the reaction zone per hour per weight of molecular sieve in the molecular sieve catalyst composition in the reaction zone. The WHSV is maintained at a level sufficient to keep the catalyst composition in a fluidized state within the reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol, dimethyl ether, or both, is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the one or more riser reactors, is at least about 0.1 meter per second (m/sec), preferably greater than about 0.5 m/sec, more preferably greater than about 1 m/sec, even more preferably greater than about 2 m/sec, yet even more preferably greater than about 3 m/sec, and most preferably greater than about 4 m/sec. See, for example, U.S. patent application Ser. No.

09/708,753, filed Nov. 8, 2000, the entirety of which is incorporated herein by reference.

C. The Feed Vaporization and Introduction System

The present invention provides for increased efficiency in the removal of impurities/contaminants in the form of non-volatiles and/or low-volatiles from a feed stream as well as increased performance in maintaining efficient temperature and pressure of the oxygenate feed. U.S. patent application Ser. No. 10/304,328, which was filed on Nov. 26, 2002, entitled "Method and Apparatus for Treating Oxygenate-Containing Feeds and Their Use in Conversion of Oxygenates to Olefins," the entirety of which is incorporated herein by reference, describes an FVI system that may be implemented according to the present invention.

A non-limiting list of exemplary non-volatile materials includes inorganic metals, salts, acids and bases, dirt, clay, sand, rust, soot, and mixtures and alloys of inorganic materials, e.g., catalyst fines. Such non-volatile materials can include organic compounds that exhibit a negligible vapor pressure at the conditions necessary to prepare a feed for the OTO conversion process. Examples of non-volatile and/or low-volatile organic compounds include asphaltenes, polymers, tars, coal, waxes, heavy oils, silicone oils and silicon polymers. Most of the non-volatile materials are either solids or viscous liquids at ambient conditions.

In addition to materials that exhibit negligible vapor pressure at the conditions necessary to prepare feed for the OTO conversion process, deleterious components that boil at temperatures significantly greater than the dominant oxygenate in the oxygenate feed may also be present in the oxygenate-containing feed. These low-volatile components may include crude oil, heavy naphthas, distillates and other petroleum fractions or blend stocks, as well as processed petroleum products, chemicals produced from petroleum products, lubricating oils, hydraulic oils, oil additives, as well as non-carbon based chemicals and inorganic chemicals including, but not limited to, those containing halogens. Many of the deleterious boilable components exhibit low vapor pressures at the conditions necessary to prepare feed for the OTO process and hence are either essentially non-volatile or low-volatile materials. Such non-volatile or low-volatile materials not only reduce or eliminate catalyst performance but can deposit on internal surfaces of the OTO conversion reactor as well as apparatuses situated downstream of the conversion reactor, e.g., the product recovery train. Many of these low-volatile or non-volatile contaminants in oxygenate-containing feeds are introduced from residual materials present in logistics systems such as ships, tanks, and pipelines employed in the storage and transportation of these feeds.

As used herein, the term "non-volatiles" means materials that have negligible vapor pressure at the conditions necessary to prepare feed for the OTO conversion process. Typically, these conditions include temperatures ranging from about 32° (0° C.) to about 500° F. (260° C.), and pressures ranging from about 20 psia (137.9 kPaa) to about 150 psia (1034 kPaa), preferably temperatures ranging from about 200° (93° C.) to about 400° F. (204° C.), and pressures ranging from about 20 psia (137.9 kPaa) to about 100 psia (689.5 kPaa), say from about 50 psia (344.8 kPaa) to about 95 psia (655.0 kPaa). These materials are thus neither sublimable nor boilable at OTO feed conditions.

For present purposes, "low-volatiles" are defined as materials having a normal boiling point (at one atmosphere pressure) at least 100° F. (38° C.) higher than the normal boiling point of the dominant oxygenate component in the feed. "Volatiles" are defined herein as materials having a normal boiling point less than 100° F. (38° C.) higher than the normal boiling point of the dominant oxygenate component in the feed. For example, dodecane has a normal boiling point of about 421° F. (216° C.), and benzene has a normal boiling point of about 176° F. (80° C.). For the purposes of this invention, if methanol, which has a normal boiling point of about 148° F. (64° C.), is the dominant oxygenate, then dodecane is a low-volatile whereas benzene is a volatile. It will be recognized by those skilled in the art that detailed calculations or experiments are possible to estimate the approximate separation of all materials in the oxygenate feed that have measurable vapor pressures. These calculations can be used to estimate the efficiency of the invention.

According to the present invention, a liquid-vapor disengaging drum receives an oxygenate-containing feed from at least one feed pre-heater and provides an effluent stream to one or more OTO reactors. Installed in a recycle loop for the drum is a heat exchange means comprising at least one heat exchanger, external to the vapor-liquid disengaging drum. In one embodiment, the heat exchanger means comprises a plurality of heat exchangers. The heat exchangers may be installed in series and/or in parallel relative to one another. In a particular embodiment, at least two heat exchangers are installed in parallel to each other in the recycle loop.

The specific heat exchanger employed can be any heat exchanger suitable for its purpose in the invention. For purposes of the present invention a heat exchanger is defined as a means for transferring heat from a heat source, such as a heat exchange fluid to a heated material, in this case the liquid effluent from the vapor-liquid disengaging drum, through a heat transferring medium located between the heat source and the heated material, such as metal. Heat transfer is thereby accomplished without physically contacting the heat source with the heated material.

Suitable heat exchangers for use herein can be selected from horizontal or vertical shell and tube exchangers configured for partial vaporization. In one embodiment, at least one exchanger comprises a circulating partial vaporizer where the circulation of the effluent liquid is either induced by at least one of: (i) mechanically pumping the effluent through the exchanger; or (ii) a thermosyphon where the weight or static head of the effluent liquid is greater than the weight or static head of the heat exchanged and partially vaporized effluent returning to the drum, thus inducing circulation through the exchanger. The circulating partial vaporizer can be situated externally to the vapor-liquid disengaging drum. Partial vaporizers utilizing mechanical pumps for circulation are preferred where the source of heat for the exchanger is either remote or in a location that does not permit the use of a thermosyphon.

Partial vaporizers can be configured to vaporize from about 5 to about 95 vol % of the circulating fluid, say, from about 20 to about 40 vol %, e.g., from about 30 to about 40 vol % of the circulating fluid. This level of vaporization generally prevents the deposition of non-volatiles and low-volatiles in the heat exchanger.

In one embodiment of the present invention, heat is supplied to the heat exchanging means, e.g., a partial vaporizer, for exchange to the liquid oxygenate-containing stream from the vapor-liquid disengaging drum from one or more of: an externally supplied steam, water from a quench operation, e.g., water used to quench an OTO conversion effluent stream (with attendant quenched products in the water), and/or the OTO conversion effluent itself. Operating plural heat exchangers located in parallel to one another provides desired flexibility. Flexibility in controlling heat exchange may further be provided by using more than one type of heat source to the heat exchanger means, e.g., providing each heat exchanger with a different type of heat source.

The heat exchanger means at least partially vaporizes the oxygenate-containing feed and delivers the at least partially vaporized feed to the vapor-liquid disengaging drum for separation into a vapor that exits the drum overhead and a liquid that optionally is combined with the preheated oxygenate feed entering the drum. The combined liquid in the drum circulates to the heat exchanging means and is at least partially vaporized again. The vapor-liquid disengaging drum approximates a theoretical single fractionation stage. The non-volatiles and low-volatiles mostly remain in the liquid concentrating to a level determined by the concentration of non-volatiles and low-volatiles in the feed and the percent by weight of the total feed withdrawn from the drum as liquid blowdown. The overall percentage by weight of the fresh oxygenate-containing feed (excluding recycle streams) vaporized in the drum is 100 wt % minus the percentage by weight of blowdown. In one embodiment, the total feed withdrawn as blowdown can range from about 1 to about 20 wt %, say, from about 1 to about 10 wt %, e.g., from about 1 to about 5 wt %. The amount of non-volatiles and low-volatiles in the vapor leaving the drum is related to the amount of unseparated liquid mist carried overhead with the vapor from the drum. The amount of non-volatiles and low-volatiles in the mist is inversely proportional to the weight percentage of blowdown. Thus, a measure of control is exercisable over the amount of non-volatiles and low-volatiles carried overhead with the vapor by increasing or decreasing the percentage of the total feed to the blowdown. The approximate concentration of non-volatiles or low-volatiles in the oxygenate liquid in the drum is subject to calculation. At some elevated concentration level in the liquid, the non-volatiles and/or low-volatiles begin to separate as a solid phase in the drum. The blowdown rate or weight percentage of fresh feed should be maintained at a sufficient level to avoid accumulations of a solid phase in the drum. Inasmuch as the properties of non-volatiles and low-volatiles can be expected to vary, a drum liquid analysis can be used to establish the blowdown weight percentage. A partial analysis of non-volatiles can be obtained using a conductivity probe, wherein ion concentration in an oxygenate liquid phase is related to conductivity. In one embodiment, the conductivity probe is installed online and may be used to control the blowdown rate.

Because the oxygenate feedstock normally is stored at ambient temperatures before use in the conversion process, the feedstock has to be heated to a higher temperature with a much higher heat content suitable for contacting the oxygenate conversion catalyst. The heat content of the feedstock can be used as a factor for varying the temperature at which the OTO conversion reactor is operated.

It is preferable to increase the heat content and/or the temperature of the feedstock through from one to about three intermediate stages, with each stage having a successively higher heat content. Many different streams in the oxygenate conversion process may be suitable sources for providing the necessary heat to increase heat contents. These streams include those derived from the heavy product fraction from the quench tower and the streams from the fractionator separating quench medium from other components. It should be pointed out that a stream may have a higher heat content after a heat exchange even though it has a lower temperature, primarily resulting from pressure changes and/ or phase changes, such as vaporization of a liquid as may occur in an OTO conversion process. In one embodiment of the invention, the reactor feed temperature is further increased in a fourth stage of heat exchange on the vapor feed to the reactor. Steam can be used as a source of heat in this stage of heat exchange.

In accordance with one embodiment of the present invention, the preheated feedstream is then fed into at least one disengaging drum capable of maintaining proper pressure and temperature for separating impurities out of the oxygenate feed. Preferably only a single disengaging drum is employed inasmuch as a single feed vapor-liquid disengaging drum with multiple heat exchanger inputs is the least complex means to approach a single theoretical stage of fractionation sufficient to reject substantially all non-heavy hydrocarbon non-volatiles and many of the heavy hydrocarbon low-volatiles as well. The oxygenate feed then needs to be at least partially vaporized and contacted in a suitable oxygenate conversion reactor with the selected molecular sieve catalyst under process conditions effective to produce the desired olefins at an acceptable conversion level with desired selectivity.

The OTO catalyst is susceptible to poisons in the oxygenate-containing feed that include rust, soot, metals, salts and heavy hydrocarbons. These poisons can incapacitate a catalyst, either temporarily or permanently, and therefore it is desirable to remove them completely from the oxygenate-containing feed to the OTO reactor.

In one embodiment of the invention, after contacting the oxygenate feedstock with the oxygenate conversion catalyst present in the OTO reactor, the oxygenate conversion reaction product effluent comprising olefin products is quenched directly by contacting a suitable quench medium in a quench tower. The compounds in the effluent stream that are gaseous under the quenching conditions are separated from the quench tower as a light product fraction for olefin product recovery and purification. The light product fraction comprises light olefins, dimethyl ether, methane, CO, $CO_2$, ethane, propane, and other minor components such as water and unreacted oxygenate feedstock. The compounds in the effluent stream that are liquid under quenching conditions, are separated from the quench tower as a heavy product fraction for heat recovery, and possible division into several fractions and separation of the quench medium. The heavy product fraction comprises byproduct water, a portion of the unreacted oxygenate feedstock (except those oxygenates that are gases under quenching conditions), a small portion of the oxygenate conversion byproducts, particularly heavy hydrocarbons ($C_6$+), and usually the bulk of the quench medium. Further details of such reactions may be found in U.S. Pat. No. 6,121,504, the entirety of which in incorporated herein by reference.

In one embodiment of the present invention wherein more than one vapor/liquid disengaging drums are utilized, the primary or controlling drum has an independent source of steam, whereas the secondary drum or drums typically do not. Typically, the secondary drums are maintained under at least the same pressure as the primary drum. The treated oxygenate feed vapor from the vapor/liquid disengaging drums is passed to the OTO reactors through the primary drum.

Referring to FIG. 1, one aspect of the invention and a number of the preferred embodiments are shown. Prior to the present invention it has been exceedingly difficult to produce a clean effluent feed that had been vaporized while still maintained at a proper pressure and temperature.

In an embodiment of the invention, the FVI process for an OTO reactor begins with an oxygenate-containing feed 2 which contains impurities, which if not at least partially removed, can deleteriously deposit on catalyst and/or on the internal surfaces throughout the apparatus of the process. One or more pumps 6 can be used to maintain or facilitate flow of the feed. The oxygenate-containing feed 2 is heated by one or more feed preheaters 8, 10 and 12 which may be arranged serially and/or in parallel, prior to being fed into a vapor-liquid disengaging drum 14 via vapor-liquid disengaging drum inlet 16.

The vapor-liquid disengaging drum 14 is the primary location where non-volatiles and/or low volatiles present in the oxygenate-containing feed are separated from volatiles, e.g., materials that are distillable and/or sublimable under the conditions used to prepare OTO feeds. The disengaging drum 14 contains a boilable fluid medium such as an oxygenate compound which is used as a heat sink to control the temperature within the vapor-liquid disengaging drum. The drum is operated so as to maintain the oxygenate feed at a predetermined temperature and pressure. The temperature and pressure levels are maintained sufficient to provide an at least partially vaporized effluent stream (or phase) and an at least partially liquid stream (or phase).

The at least partially vaporized effluent stream is passed through drum outlet 18, optionally through an optional wash column demister 20 comprising packing and demister screens 22 and 24 and having an upper inlet 26 for a wash column demister liquid oxygenate reflux 28 and eventually fed as vapor via line 30 into an OTO reactor, not shown, and/or directed via valve 32 to an upper inlet 34 of condenser 36 having a bottoms outlet 37 through which liquid condensed oxygenate is passed to pump 38 for transmission to condenser recycle inlet 40, to wash column demister 20 as a demister wash column wash via reflux 28, and/or to an OTO reactor via line 42. Thus, in one embodiment of the invention, a liquid feed is fed into the OTO reactor. This liquid feed should be free of non-volatiles and, preferably, low-volatiles and kept close to its vapor point. The liquid feed is used to control the temperature in the OTO reactor and the proportion of vapor to liquid feed used is dependent on the OTO reactor conditions as described above. The wash column demister 20 will further remove any entrenched non-volatiles.

An at least partially liquid stream (or phase) from the vapor-liquid disengaging drum is passed through a vapor-liquid disengaging drum liquid stream outlet 44 via line 46 to a heat exchanger means. The heat exchanger means can comprise a plurality of partial vaporizers 48, 50 and 52, respectively, installed in parallel inlet lines 54, 56 and 58, respectively. Heat is thus added to the at least partially liquid stream and a heated at least partially vapor stream removed from the heat exchangers via lines 60, 62 and 64, thence through line 66 to a second inlet 68 to the vapor-liquid disengaging drum 14. Heat is supplied to the partial vaporizers 48, 50 and 52, via hot OTO reactor effluent 49, steam 51, and/or hot quench liquid 53 resulting from quenching OTO reactor effluent, e.g., using quench water. Heat input to the heat exchangers is controlled so as to provide a heat exchanged vapor phase oxygenate-containing stream of sufficient heat content as vaporized feed via drum outlet 18 for OTO reactor requirements.

In one aspect of the invention, the vapor phase is removed through drum outlet 18. The vapor phase is free of non-volatiles and, preferably, low-volatiles except for liquid phase mist carried with the vapor phase through outlet 18. The majority of the non-volatiles and low-volatiles accumulate in the liquid phase and can be removed from the disengaging drum as blowdown via blowdown outlet 70. These non-volatiles and low-volatiles may be disposed of in a variety of useful manners known in the art. In one embodiment volatiles trapped in the blowdown are removed by conveying blowdown via pump 72 to the top of condensate stripper 74 via line 75. Alternatively, the blowdown can be conveyed to the condensate stripper through intermediate condensate stripper inlet 76, particularly in those instances where an alternate source of reflux is made available to the top of the condensate stripper as discussed below. The condensate stripper 74 is heated by a condensate stripper bottoms heat exchanger 78 wherein heat is added to at least a portion of the bottoms taken from condensate stripper outlet 80 via line 82. The heated bottoms are returned to the condensate stripper via line 84. The bottoms, which contain water, heavy hydrocarbons, non-volatiles and low-volatiles, may be removed via line 81 to a disposal or recycle system, not shown, which may include a water treatment plant. In one embodiment, the solids and heavy hydrocarbons from the blowdown can be directed to heavy oil removal and separation systems included with the aforementioned quench systems used to treat oxygenate to olefins reactor effluent.

Condensate containing oxygenates, e.g., methanol and water, such as that provided by quenching an OTO reactor effluent as discussed above can be separately added to condensate stripper 74 via intermediate condensate stripper inlet 86. Condensate stripper overhead is removed from the condensate stripper by line 88 and recycled to the vapor-liquid disengaging drum 14 through vapor-liquid disengaging drum inlet 90. In one embodiment, at least a portion of the overhead from line 88 is directed through line 92 controlled by valve 94 to a condensate stripper overhead condenser drum 96, which separates out non-condensables from condensable liquids. This condensate stripper overhead condenser drum 96 is separate from the vapor-liquid disengaging drum 14. A vapor-containing stream is taken off the condensate stripper overhead condenser drum 96 through line 98, and a liquid-containing stream is taken via line 100 and preferably is directed by reflux pump 102 to i) the top of condensate stripper 74 via line 104 and/or ii) an OTO reactor inlet via lines 105 and 42. Regulating the flow of these liquid-containing streams via lines 105 and/or 42 can be used to control temperature in the OTO reactor. These liquid-containing streams that contain extremely low levels of at least low-volatile contaminants are thus well-suited as feeds to the reactor. The vapor-containing stream can be subsequently flared or utilized as fuel. In an alternate embodiment, at least a portion of the condensate stripper overhead is directed via line 89 to vaporized effluent in line 30 and introduced into the OTO reactor. This is particularly suited where reflux to the condensate stripper 74 is provided by an alternate oxygenate-containing stream such as blowdown from the vapor-liquid disengaging drum 14.

In a particular embodiment of the present invention, an OTO reactor effluent, e.g., reactor effluent 49 is taken via line 106 to a reactor effluent quench unit 108 whose bottoms can be directed to condensate stripper 74 via line 110 and intermediate condensate stripper inlet 86. Quench unit overhead containing olefins is taken via line 112 to initial olefin recovery unit 114 and thence via line 116 to a product recovery wash system 118, e.g., a column, to which water or oxygenate-containing wash is fed via line 120 to remove water and/or oxygenates. Typically, an oxygenate-containing wash can be derived from oxygenate feed, condensate, boiler feed water, process water or product oxygenates, as well as other suitable sources. The oxygenates in the wash extract may be recovered and purified as feed for the OTO reactor. Wash extract is removed via line 124 and directed to quench tower 108 or condensate stripper 74. Washed overhead is taken via line 126 to additional olefins recovery unit 128 to form one or more final product streams, not shown.

D. Shipping Methanol in Non-Methanol Carriers

U.S. patent application Ser. No. 10/304,409 (the "'409 application"), which was filed on Nov. 26, 2002, entitled "Shipping Methanol for a Methanol to Olefin Unit in Non-Methanol Carriers," the entirety of which is incorporated herein by reference, describes processes for converting a conventional tanker to a tanker suitable for carrying methanol that is to be used in a methanol to olefin reaction system. One or more of non-volatile contaminants, e.g., soot and rust; low-volatile contaminants, e.g., heavy hydrocarbons; and/or volatile contaminants, e.g., $SO_x$, carbonic acid, and C5-hydrocarbons, may be introduced into an oxygenate-containing feed from tankers modified by the processes described in the '409 application. The FVI system of the present invention, described above, is particularly well suited for selectively removing non-volatile and low-volatile contaminants from an oxygenate-containing feed that has been transported by tankers modified by the processes described in the '409 application. The volatile contaminants $SO_x$, carbonic acid, and C5-hydrocarbons do not significantly affect catalytic activity or the MTO reaction process and may be allowed to enter the MTO reactor.

It has been discovered that a methanol feedstock for an MTO process unexpectedly need not be of as high quality as methanol for non-MTO processes. Contaminants in methanol resulting from uncoated tanker holds and/or from a blanketing medium will not significantly impact the MTO process. Therefore, when using ships with tank holds greater than 3,000 $m^3$ in volume, a non-nitrogen blanketing system is sufficient to satisfy the SOLAS resolution and deliver an acceptable MTO feedstock. Crude and naphtha-carrying tankers are plentiful and generally much less expensive to build or modify than conventional large methanol-carrying tankers because they typically do not have coated holds or expensive inerting systems. As used herein, "naphtha" means a gasoline material containing C5+ hydrocarbons. A non-limiting list of exemplary naphthas includes refined gasoline, raw gasoline, natural gasoline, and field condensates. The costs associated with shipping methanol destined for an MTO reactor system may be greatly reduced from conventional methanol shipping costs by modifying a conventional crude or naphtha-carrying tanker to carry MTO grade methanol.

In one embodiment, a relatively inexpensive process is provided for modifying conventional crude/naphtha-carrying tankers to ship MTO grade methanol. The process includes one or more of the following steps: (1) cleaning the holds of the crude/naphtha-carrying tanker to remove residual deposits, wherein the holds previously stored a non-methanol material; (2) providing a fire suppression system specially designed to prevent methanol fires; and (3) replacing methanol intolerant pump seals and flange gaskets in the tanker with methanol resistant seals and gaskets. The fire suppression system includes a fire suppression conduit system for delivering the alcohol resistant fire suppression agent to the tanker holds.

A methanol blanketing system is also provided, which includes a blanketing medium generator in a tanker for generating a blanketing medium selected from the group consisting of: exhaust gases from a diesel engine, a gas oil engine, a kerosene engine, a gasoline engine and a methanol engine. Additionally or alternatively, the blanketing medium generator is a diesel, gas oil, kerosene, methanol or gasoline burner having a combustion chamber, or any other fuel burning engine or burner. Both the engine and the burner style blanketing medium generators provide a satisfactory blanketing medium, which optionally includes water-saturated carbon dioxide. A conduit system is also provided, which is in communication with the blanketing medium generator and one or more holds. The blanketing medium generator directs the blanketing medium through the conduit system to the one or more holds, the holds being at least partially filled with a fluid cargo comprising methanol.

Additionally, a process is provided for unloading methanol from a tanker. The process includes withdrawing at least a portion of the methanol from a hold, and replacing the volume of the withdrawn methanol with a blanketing medium. The blanketing medium is selected from the group consisting of: exhaust from a diesel, gas oil, kerosene, methanol, or gasoline engine. Additionally or alternatively, the blanketing medium is provided by a diesel, gas oil, kerosene, methanol or gasoline burner. The blanketing medium may include carbon dioxide, carbon monoxide, soot, $SO_x$, particulate contaminants or a combination thereof.

In one embodiment, the present invention is directed to a process for modifying a tanker for carrying methanol destined for use as a feedstock in an MTO reaction system. The process includes: (1) cleaning the holds of the crude/naphtha-carrying tanker to remove residual deposits; (2) providing a fire suppression system for delivering an alcohol-resistant fire suppression agent; and (3) replacing methanol intolerant seals and/or gaskets in the tanker with methanol resistant seals and/or gaskets. The process optionally includes providing a blanketing system, which delivers a blanketing medium to the holds. In another embodiment, the invention is directed to a process for converting methanol to light olefins wherein the methanol does not pass specification for Grade A or AA methanol. In other embodiments, the invention is directed to a tanker modified by the above process, a methanol blanketing system, a process for unloading methanol from a tanker, and a process for providing methanol to an MTO reaction system.

The reaction of methanol to olefins, described in more detail above, involves contacting methanol with a molecular sieve catalyst under conditions effective to convert at least a portion of the methanol to light olefins, e.g., ethylene and propylene. It has been discovered that a methanol-containing stream containing a certain level of contaminants surprisingly may be, depending on the type and amount of contaminant, provided directly to an MTO reaction system without significantly affecting the MTO reaction process. More specifically, it has been discovered that the catalysts implemented in the MTO reaction process will not be significantly deactivated by select volatile contaminants such as $SO_x$, carbonic acid, and $C_5$-hydrocarbons. Vaporization of the methanol-containing feedstock prior to its introduction into an MTO reactor also limits particulate and salt contamination or contamination by other non-volatile components, as described above. Thus, one embodiment of the present invention is directed to a process for converting methanol in a dirty methanol stream to light olefins. A "dirty" methanol stream is defined herein as a methanol-containing stream that does not pass specification for Grade AA methanol. Grade AA methanol is a methanol-containing stream that passes certain federally prescribed tests. Grade A methanol may contain more contaminants, e.g., water, than Grade AA methanol and is also defined by federally prescribed tests. The table below provides the requirements for Grades A and AA methanol.

TABLE 1

Tests and Requirements for Grades A & AA Methanol

| Test | Grade A | Grade AA |
| --- | --- | --- |
| 1. IMPCA 001 Methanol | 99.85 wt. % Min. | 99.85 wt. % Min. |
| 2. ASTM D346 Water | 1500 ppm wt. Max. | 1000 ppm wt. Max. |
| 3. ASTM D1209 Color | 5 mg pt/liter Max. | 5 mg pt/liter Max. |
| 4. ASTM D1078 Distillation | 149° F. ± 0.9 | 149° F. ± 0.9 |
| 5. ASTM D1363 $KMnO_4$ test at 68° F. | 30 minutes | 30 minutes |
| 6. ASTM D1722 Hydrocarbons | Pass test | Pass test |
| 7. Visual Appearance | Clear & Colorless | Clear & Colorless |
| 8. ASTM D891 Specific Gravity @ 68° F. | 0.791–0.792 | 0.791–0.792 |
| 9. ASTM D1613 Acid Number | <0.03 mg KOH/g | <0.03 mg KOH/g |
| 10. ASTM E346 Carbonyl number | <0.02 mg KOH/g | <0.02 mg KOH/g |
| 11. ASTM D3961 Sulfur | 0.5 ppmw | 0.5 ppmw |

An important advantage of the present discovery is that a non-conventional methanol tanker, which might cause contamination of the methanol stored therein, may be used to transport methanol destined for an MTO reaction system, particularly if the tanker is modified according to the present invention. Although the methanol unloaded from these modified tankers may contain one or more volatile, non-volatile and/or low-volatile contaminants, the methanol is still suitable for an MTO reaction system. The tanker may or may not have previously carried a non-methanol material, such as naphtha or crude oil.

One embodiment of the present invention is a process for modifying a tanker to carry methanol. The process includes providing a tanker having one or more holds that previously stored and/or was designed to hold a non-methanol material. A fire suppression system is provided for delivering an alcohol resistant fire suppression agent to the holds. The fire suppression system preferably includes a conduit system for delivering the alcohol resistant fire suppression agent to the holds. The time required to accomplish the conversion on an existing standard Aframax product carrier is 2 to 5 months depending on the design of the ship.

Conventional fire suppression systems for tankers that are designed to carry a non-methanol cargo, e.g., naphtha or crude oil, typically include a fire suppression system storage tank, a pump and conduit lines, e.g., pipes, which transfer the fire suppression agent to outlet nozzles, e.g., turrets, which optionally are used to direct the suppression agent at a fire in one or more of the holds. Typically, the fire suppression agent for a non-methanol carrying tanker is a protein based or AFFF foam extinguishing material, which may be ineffective or unsatisfactory against a methanol fire. Specifically, alcohols may break down these conventional fire suppression agents causing them to reduce their extinguishing characteristics. The IBC code dictates the requirements for methanol fire suppression including the type and amount of foam required. Thus, in one embodiment of the invention, the fire suppression system is supplemented, replaced or modified to allow the suppression system to adequately deliver an alcohol-resistant fire suppression agent to the tanker holds.

A preferred alcohol-resistant fire suppression agent is a foam material, such as UNITOL fire suppression foam marketed by Unitor ASA (Oslo, Norway). The UNITOL fire suppression foam or other fire suppression foam to be implemented according to the present invention ideally has an increased surface tension so the foam preferably will not break apart when it contacts methanol. Specifically, the foam fire suppression agent preferably includes a surfactant, which prevents the foam from breaking up upon its release onto a methanol fire. Because foam materials are less dense than conventional fire suppression agents used in non-methanol carrying tankers, the tanker's fire suppression system should be modified in order to be able to adequately deliver the foam fire suppression agent to the tanker holds. Approximately twice as much alcohol resistant fire suppression agent than conventional fire suppression agent may be required. Accordingly, in accordance with the present invention, a fire suppression agent storage tank having increased volume should be provided that is capable of storing an alcohol-resistant fire suppression agent. The existing tank may be enlarged through well known techniques, or supplemented with an additional fire suppression agent storage tank. Alternatively, the existing tank is removed and replaced with a larger storage tank better suited for storing an alcohol-resistant fire suppression agent.

Similarly, the conduit lines for transferring the fire suppression agent to the one or more outlets should be modified, supplemented with a second conduit system or replaced with a second conduit system to provide a final conduit system capable of delivering the alcohol-resistant fire suppression agent to the outlets and, ultimately, to the holds or tanker deck at a satisfactory flow rate to enable the extinguishing of a methanol fire. Preferably, the overall cross sectional area of the final conduit system will be larger than the preexisting conduit system in order to allow an increased flow capacity necessary for delivering a foam fire suppression agent to the outlets. Additionally or alternatively, the existing fire suppression conduit lines may be supplemented with an additional set of conduit lines to enable satisfactory delivery of the methanol-resistant fire suppression agent to the outlets.

The tanker also will likely have a preexisting pump adapted to deliver a liquid fire suppression agent to the conduit system. Pumping an alcohol-resistant fire suppression agent with the preexisting pump may not provide sufficient flow characteristics for the alcohol-resistant fire suppression agent. Accordingly, in one embodiment of the present invention, the preexisting pump is replaced with a second pump adapted to pump the alcohol-resistant fire suppression agent at a sufficient volumetric flow rate. The second pump is adapted to pump the alcohol-resistant fire suppression agent from the storage tank to the conduit system and, ultimately, to the outlets and holds. In another embodiment, the preexisting pump is supplemented by a second pump, and the two or more pumps will operate simultaneously or intermittently in order to provide desirable pumping characteristics for the alcohol-resistant fire suppression agent. In another embodiment, the preexisting pump is modified, e.g., by increasing the size of the impeller, in order to provide desirable pumping characteristics for the alcohol-resistant fire suppression agent.

The fire suppression system optionally includes one, two, three, four or more fire suppression agent outlets. Each outlet preferably is an aimable turret adapted to direct and deliver the alcohol-resistant fire suppression agent toward the one or more holds or the tanker deck in order to extinguish any methanol fire present. Each turret preferably may be controlled by an individual who is able to aim the turret at a fire in one or more of the holds or on the deck of the tanker. Alternatively, a remote operating system is provided to operate the turret. In one embodiment, the preexisting nozzles are adapted to deliver the alcohol-resistant fire suppression agent. For example, the preexisting nozzles may be removed, replaced or modified with nozzles capable of delivering the alcohol-resistant fire suppression agent to the holds or the tanker deck. Each turret should be modified to include a nozzle creating a sufficient flow rate for the alcohol-resistant fire suppression agent. The fire suppression system also optionally includes one, two, three, four or more fire suppression agent turrets with modified nozzles.

In addition to providing a fire suppression system capable of delivering an alcohol-resistant fire suppression agent, the process for modifying a tanker to carry methanol preferably includes providing a gas blanketing system or an inerting system. A gas blanketing system is a system for delivering a gas blanketing medium to one or more of the tanker holds. The gas blanketing medium optionally comprises exhaust from a gasoline, kerosene, gas oil, methanol or diesel burning engine. Additionally or alternatively, the blanketing medium is provided by a diesel, gas oil, kerosene, gas oil, methanol or gasoline burner. A blanketing medium from a burner is referred to as flue gas. For tankers carrying methanol, a gas blanketing system is particularly desirable in order to reduce the amount of oxygen that contacts the methanol thereby decreasing the risk of a methanol fire. During the unloading of the methanol cargo, the blanketing medium is fed into the hold to replace the volume of methanol that is removed from the tanker hold.

An inerting system is a type of gas blanketing system wherein an inert gas, referred to generally as an inerting medium, such as nitrogen, acts as the blanketing medium. For example, in an inerting system, a nitrogen generator may be provided to supply nitrogen to the one or more holds. Nitrogen inerting systems, although more expensive than other blanketing systems, are well-known to be desirable for large methanol tankers because the inert gas does not impart contaminants to the methanol. Ships having tank holds smaller than 3,000 $m^3$ are not required by the SOLAS resolution to blanket methanol with a blanketing medium, and hence do not incur the cost of providing a blanketing system.

As it has been discovered that a dirty methanol stream may be effectively directed to an MTO reaction system, a tanker that previously carried or was designed to carry a non-methanol cargo may be modified to carry methanol destined for an MTO reaction system by providing a gas blanketing system including a gasoline, kerosene, gas oil, diesel or methanol burning engine or a diesel, gas oil, kerosene, methanol or gasoline burner. The blanketing medium from the engine or burner is directed to the one or more methanol-containing holds. Although the blanketing medium from an engine or burner, depending on the fuel, will contain components such as CO, $CO_2$, and $SO_x$ and soot that will contaminate the methanol stored in the holds, the contaminated methanol is surprisingly still suitable for serving as a feedstock for an MTO reaction system. Specifically, soot and other particulates are caught in an on-site tank system or in the blowdown stream of the FVI system, discussed above. Unburned $C_5$-hydrocarbons and sulfur are in small enough quantities as not to be considered an issue. Secondary contaminants, which are formed from one or more of these contaminants, also may contaminate the methanol stored in the holds, although the methanol is still suitable for use in an MTO reaction system. For example, $CO_2$ in methanol may form a secondary contaminant such as carbonic acid, which vaporizes with the oxygenate feed in the FVI system. However, the presence of carbonic acid with the vaporized oxygenate feed does not render the methanol cargo unsuitable for use in an MTO reaction system. Unlike conventional methanol-implementing processes such as MTBE and formaldehyde syntheses, the methanol feed preheat and vaporization section of an MTO reaction system, discussed in detail above, will vaporize methanol away from soot particles and other non-volatiles contained in the feedstock. Limited amounts of volatiles such as $SO_x$, CO, carbonic acid and $C_5$-hydrocarbons may vaporize with the methanol and be transported to the reactor without significant detrimental effects on conversion or catalyst activity. Accordingly, if an unmodified tanker includes a gas blanketing system wherein the blanketing medium was exhaust or flue gas from a gasoline, kerosene, gas oil, or diesel engine or burner, the invention comprises placing methanol in the one or more holds and blanketing the methanol with the exhaust or flue gas from the gasoline, kerosene, gas oil or diesel engine or burner. The invention also includes selectively removing non-volatile contaminants, e.g., soot and rust, from the oxygenate feed, as discussed above. Unlike conventional large methanol-carrying tankers, the methanol is stored for transportation under a blanketing medium wherein the blanketing medium is exhaust from an engine or flue gas from a burner rather than nitrogen from a nitrogen generator. The blanketing medium generator optionally is upgraded by installing scrubbers to reduce the amount of soot, moisture, particulates and $SO_x$ in the gas to be used as the blanketing medium.

In another embodiment, the tanker is provided with an inerting system wherein the blanketing medium is an inert gas such as nitrogen. In this embodiment, the inerting system comprises an inerting medium generation unit, e.g., a nitrogen generator, which provides the inerting medium. The inerting system optionally is connected to a preexisting gas piping system thereby reducing installation costs.

Optionally, the tanker is provided with a methanol engine or burner, which forms exhaust or flue gas that serves as the blanketing medium. A blanketing medium from a methanol engine or burner is particularly clean and will not significantly contaminate the methanol cargo. In this embodiment, a small portion of the methanol cargo may be provided as fuel for the methanol engine or burner. One or more pumps, control devices and conduit lines may be provided to transport methanol from the one or more holds to the methanol engine or burner fuel tank or directly to the methanol engine or burner.

Regardless of the type of blanketing medium (engine exhaust, flue gas, inert gas or other blanketing medium), the blanketing system preferably includes one or more conduit lines, pumps and control devices for directing the blanketing medium to the one or more holds. If the tanker includes a plurality of laterally oriented holds, the blanketing system preferably includes at least two longitudinally extending conduit lines, which direct the blanketing medium to the holds. Each conduit line includes at least one outlet for each respective hold. The blanketing medium is directed through the lines and exits the conduit lines via the outlets. Optionally, the conduit line or lines include a plurality of outlets, e.g., 2, 3, 4 or more, for each respective hold.

Thus, one embodiment of the present invention is a methanol blanketing system including a blanketing medium generator, e.g., a diesel, gasoline, methanol, gas oil, or kerosene engine or burner, in a tanker for generating a blanketing medium. The blanketing medium is selected from the group consisting of exhaust from a diesel engine, exhaust from a kerosene engine, exhaust from a methanol engine, exhaust from a gas oil engine, and exhaust from a gasoline engine. Additionally or alternatively, the blanketing medium is selected from the group consisting of flue gas from a diesel burner, flue gas from a kerosene burner, flue gas from a methanol burner, flue gas from a gasoline burner, and flue gas from a gas oil burner. Thus, the blanketing medium can include carbon dioxide, carbon monoxide, soot, $SO_x$, particulate contaminants and combinations thereof.

Another embodiment of the present invention is a process for unloading methanol from a tanker. The process includes withdrawing methanol form a hold and replacing the volume of withdrawn methanol with a blanketing medium selected from the group consisting of exhaust from a diesel engine, exhaust from a kerosene engine, exhaust from a gas oil engine, exhaust from a gasoline engine, and exhaust from a methanol engine. Additionally or alternatively, the blanketing medium is selected from the group consisting of flue gas from a diesel burner, flue gas from a kerosene burner, flue gas from a methanol burner, flue gas from a gasoline burner, and flue gas from a gas oil burner. Thus, the blanketing medium may include carbon dioxide, carbon monoxide, soot, $SO_x$, particulate contaminants and combinations thereof.

Many non-methanol materials, such as crude and naphtha, leave hydrocarbon deposits on the inner surface of tanker holds after the material has been unloaded therefrom. Although a certain level of contaminants is acceptable for methanol destined for an MTO reactor, ideally the level of hydrocarbon contaminants is minimized. Accordingly, the process for modifying a tanker to carry methanol also preferably includes cleaning the one or more holds with a cleaning agent to remove residual deposits formed by the non-methanol cargo. Ideally, the holds are first washed, e.g., hydroblasted at about 5,000 psi or mechanically washed at about 300 psi, with a first cleaning agent. The first cleaning agent preferably comprises water. The holds are then washed with a second cleaning agent comprising an emulsifier, such as GYRO Voyage Clean, a high solvency base emulsifier and cleaner with oil-sea water emulsification abilities. After being washed with the emulsifier, the emulsifier is rinsed from the holds with a water rinse. The first and second cleaning agents and the water rinse preferably are delivered to the tanker holds with a cleaning device such as a "Butterworth" system. If necessary, the internal surfaces of the holds may be hand washed and/or further chemically cleaned. The bottoms of the tanks may also be "mucked" of all residual hydrocarbons. All slops generated during the hold cleaning process above would need to be removed and disposed of properly. Approximately 800 tons of slops will be generated for a standard Aframax vessel in crude oil service. A wall test is preferably performed after the holds have been washed by the above-described process. The downtime for cleaning the holds is 1 to 3 weeks although no downtime would be incurred for cleaning if the tanker is cleaned during repositioning. Limited residual hydrocarbon contamination of the methanol will not significantly effect conversion or catalyst activity in an MTO reaction system. Naphtha includes volatile light ($C_5-$) hydrocarbons and heavy ($C_6+$) hydrocarbons, which typically are low volatiles. Limited amounts of the light hydrocarbons may vaporize in the FVI system with the methanol and be transported to the reactor without significantly detrimental effects on conversion or catalyst activity. The methanol should vaporize away from the low-volatile heavy hydrocarbon contaminants in the MTO feed vaporization system thereby separating the heavy hydrocarbons from the methanol feedstock destined for the MTO reactor.

Unlike conventional methanol-carrying tanker holds, which are coated with a protective layer comprising zinc, holds in tankers designed to carry crude or naphtha are typically formed of uncoated carbon steel or coated with epoxy, which may break down in the presence of methanol thereby contaminating the methanol cargo. In accordance with the present invention, a methanol cargo is directed to the one or more uncoated tanker holds, zinc clad or, less desirably, epoxy-coated holds. Although the uncoated inner surface of the one or more tanker holds formed of carbon steel may impart discoloring contaminants such as rust (iron oxide) or leached metals to the methanol, it has been discovered that methanol stored in uncoated carbon steel holds is still acceptable for use as a feedstock in an MTO reaction system due to the advantageous separating ability of the FVI system, discussed in detail above. Specifically, the discoloration caused by these contaminants is not an issue for an MTO reaction system, which may also utilize uncoated carbon steel piping. Additionally, unlike conventional methanol-implementing processes such as MTBE and formaldehyde syntheses, the methanol feed preheat and vaporization section of an MTO reaction system will vaporize methanol away from soot particles, rust and other non-volatiles contained in the feedstock. Similarly, although an epoxy coating layer may break down in the presence of methanol, methanol contamination therefrom does not render the methanol cargo unsatisfactory for use as a feedstock in an MTO reaction system. Optionally, any existing epoxy coating layer is blasted off of the cargo holds thereby providing holds having uncoated inner surfaces.

Conventional crude and naphtha carrying tankers include cargo pumping systems comprising cargo pumps, which, when desired, pump the cargo out of the holds and off the tanker into on-shore storage tanks. The cargo pumps preferably include bronze or Ni—Al-Bronze casings, which are acceptable for use with a methanol cargo. However, carbon steel or stainless steel (SCS 14) internals and ductile cast iron casings are preferred. If fitted, mechanical seals are to be retrofitted with stainless steel components and buna N or EPDM elastomers. Control valves are submerged within each hold and are remotely operable to allow the cargo to be pumped out of the holds and through conduit lines to the on-shore storage tanks. These control valves are typically controlled hydraulically. The hydraulic system, which causes these valves to open, uses a hydraulic oil comprising hydrocarbons, which may leak into the holds causing hydrocarbon contamination of the methanol. In contrast, conventional methanol carrying tankers include a non-hydraulic mechanical or contained hydraulic mechanical means for removing methanol therefrom. Although hydrocarbon contamination may result from implementing a hydraulic control valve system with a methanol cargo, the resulting contaminated methanol is acceptable for use as a feedstock in an MTO reaction system for the reasons discussed above regarding residual crude and naphtha hydrocarbon contamination of methanol. Nevertheless, the control valves optionally include one or more alcohol intolerant seals or gaskets, which may break down in the presence of methanol thereby causing control valve failure and significant hydrocarbon contamination. Thus, one embodiment of the present invention includes replacing these alcohol intolerant seals and gaskets with alcohol resistant seals and gaskets. Ideally, all flange gaskets, slip type coupling joints, manhole and access hatch gaskets should be refit with materials suitable for methanol service. Preferably, the alcohol resistant seals and gaskets are formed of synthetic fiber with nitrile binder or an equivalent thereof.

Additionally, one or more preexisting ladders that provide for entry into the one or more holds may be coated or uncoated. Uncoated carbon steel ladders or ladders coated with epoxy, although subjecting the methanol cargo to contamination, will not render the methanol cargo unfit for use as a feedstock in an MTO reaction system. Optionally, the ladders are blasted to remove any coating thereon, or the ladders are retrofitted with SUS 316 stainless steel (minimum 22 mm square bar).

The process for modifying a crude or naphtha carrying tanker to carry methanol may be implemented in tankers of all sizes having varying ratings for dead weight tonnage (DWT). Preferably, the present invention is implemented in an Aframax size tanker rated at 75,000 to 125,000 DWT, although the invention may be implemented in a Suezmax tanker rated at 125,000 to 180,000 DWT, a very large crude carrier (VLCC) rated at 200,000 to 300,000 DWT or an ultra large crude carrier (ULCC) rated at 300,000 to 500,000 DWT. The invention also can be implemented in smaller tankers such as Panamax tankers rated at 45,000 to 65,000 DWT, Handy Size tankers rated at 20,000 to 30,000 DWT, or Handymax tankers rated at approximately 35,000 DWT. However, in these smaller tankers, a gas blanketing system is unnecessary. The total deadweight tonnage of the modified tanker may be at least 20,000; 35,000; 70,000; or at least 125,000 DWT.

Figure 2:
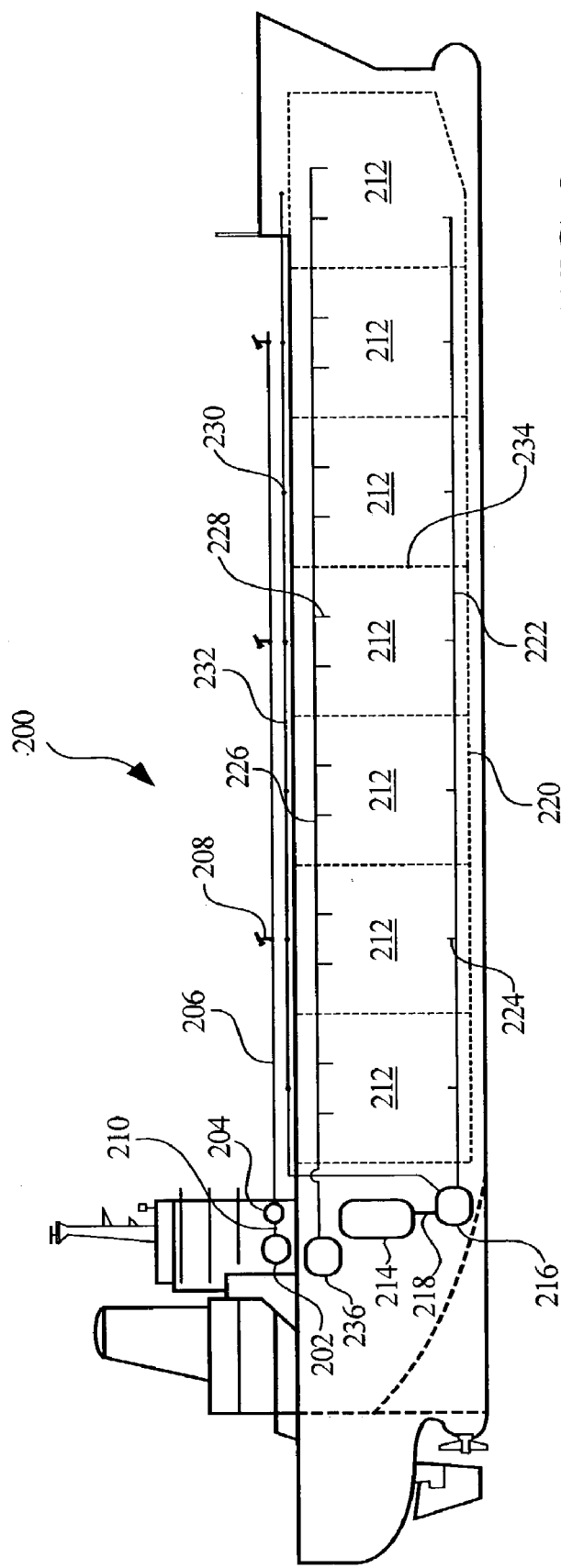
FIG. 2 illustrates a partial cross-sectional side view of a tanker that has been modified to carry methanol destined for a methanol-to-olefin reaction system.

FIG. 2 illustrates a tanker, generally designated 200, that has been modified by the above-described process. Tanker 200 includes a plurality of uncoated holds 212 for storing methanol. Each hold includes side surfaces 234 defining the side limits thereof and separating a hold from an adjacent hold. Each hold also includes a bottom surface 220 defining the bottom limit thereof. The side surface 234 and the bottom surface 220 are preferably formed of an uncoated material such as carbon steel.

The modified tanker 200 includes a fire suppression system adapted to provide an alcohol-resistant fire suppression agent to the one or more holds 212 or the tanker deck. The fire suppression system includes a fire suppression agent storage tank 202, which stores the fire suppression agent. The storage tank 202 includes a pump line 210 in fluid communication with pump 204. In the event of a fire in one or more of the holds or on the deck of the tanker 200, the pump 204 is activated to pump the alcohol-resistant fire suppression agent from the storage tank 202 through the pump line 210 and pump 204 and into fire suppression header line 206. Header line 206 directs the fire suppression agent to one or more, preferably a plurality of, fire suppression agent outlets 208. FIG. 2 illustrates three fire suppression agent outlets 208, each of which is an aimable turret. In the event of a fire, a remote control mechanism or an individual directs one or more of the aimable turrets towards the fire in order to extinguish it.

FIG. 2 also illustrates a cargo pumping mechanism adapted to pump the methanol cargo off of the ship or to circulate the methanol through the holds 212. The cargo pumping mechanism includes a methanol intake line 222, which extends longitudinally through the tanker holds 212. Although the intake line 222 is illustrated internally with respect to the holds 212, the intake line could be oriented externally to the holds 212. The intake line 222 includes a plurality of methanol inlets 224, each inlet being adapted to receive methanol from a respective hold. FIG. 2 illustrates one methanol inlet 224 per hold 212 although a plurality of inlets 224 may be oriented with respect to a single hold 212. Pump motor 214 operates on motor shaft 218 to power cargo pump 216. Cargo pump 216 creates a pressure drop on methanol intake line 222 thereby causing methanol to be supplied thereto through methanol inlet 224. The methanol received in methanol inlet 224 flows through methanol intake line 222, through pump 216 and into methanol discharge line 232. Methanol discharge line 232 is also longitudinally oriented with respect to tanker 200 and extends over the top of the holds 212. The discharge line 232 includes a plurality of methanol outlets 230, which optionally are in fluid connection with a series of external conduit lines for unloading the methanol from tanker 200. Alternatively, the outlets 230 may extend inside each enclosed hold 212 and discharge the methanol back into the holds 212 thereby providing for cargo circulation between the holds.

A gas blanketing system is also shown including a gas blanket medium generator 236. The gas blanket medium generator 236 may be a gasoline, kerosene, methanol, or diesel burning engine or an inert gas generator such as a nitrogen generator. The gas blanketing medium from gas blanket medium generator 236 is directed through gas blanket conduit line 226, which extends longitudinally over each of the enclosed holds 212. The conduit line 226 directs the gas blanketing medium to a plurality of blanket outlets 228, each of which extends inside a respective enclosed hold 212. In this manner the gas blanketing medium is directed to each of the holds 212. Two blanket outlets 228 are shown in FIG. 2 for each hold 212 although each hold may have a single blanket outlet or more than two blanket outlets.

As indicated above, a methanol-containing stream that does not pass specification for Grade A or Grade AA methanol may be fed, depending on the level and type of contaminant, directly to an MTO reaction system. For example, it has been discovered that contaminants from a gas blanketing system or from the uncoated inner surface of one or more conduit lines or holds will not render methanol unsuitable for an MTO reaction process. Accordingly, another embodiment of the present invention is a process for converting methanol to light olefins. The process includes providing a feedstock comprising methanol and a contaminant and contacting the methanol with a catalyst in a reactor under conditions effective to convert at least a portion of the methanol to the light olefins. The feedstock does not pass specification for Grade A or AA methanol. Optionally, the contaminant is selected from the group consisting of: soot, rust, $SO_x$, $CO_2$, carbonic acid, and hydrocarbons, e.g., C5-hydrocarbons.

Methanol that is stored in an unlined tank such as a conventional tanker hold will likely receive contaminants from the metal surfaces thereof. For example, rust (iron oxide) on the inner surfaces of the tank or hold may break away from the inner surface thereby contaminating the methanol with rust particles. These rust particles may cause the methanol to fail specification for Grade A or Grade AA methanol. More specifically, rust may cause the methanol to fail one or more of tests ASTM D1363, ASTM D1613, ASTM E346 and the visual appearance test for Grade A or AA methanol.

Also, the gas blanketing system may contribute to the contamination of methanol causing the methanol to fail specification for Grade A or Grade AA methanol. More specifically, soot from the blanketing medium may cause the methanol to fail one or more of test ASTM D11209 or the visual appearance test for Grade A or AA methanol. Additionally, $CO_2$ from the blanketing medium may cause the methanol to fail test ASTM D1363 for Grade A or AA methanol. The $CO_2$ may form carbonic acid in methanol, which can cause the methanol to fail test ASTM D1363 for Grade A or AA methanol. Additionally, $SO_x$ from the blanketing medium may cause the methanol to fail test ASTM D3961 for Grade A or AA methanol.

As indicated above, hydrocarbons from hydraulic oil or from deposits on the inner surface of the one or more of the holds may also contribute to the contamination of methanol causing the methanol to fail specification for Grade A or Grade AA methanol. More specifically, the hydrocarbons from the hydraulic oil or deposits from a previous non-methanol cargo may cause the methanol to fail one or more of tests ASTM D1722 and the visual appearance test for Grade A or AA methanol.

A tanker modified by the above-described invention may cause the contamination of methanol stored therein causing the methanol to not pass specification for Grades A or AA methanol. However, the present invention of converting methanol in a methanol-containing feedstock to light olefins, wherein the feedstock does not pass specification for Grade A or AA methanol, is not limited to a methanol-containing stream that has been unloaded from a tanker modified by the above-described processes.

Another embodiment of the present invention is directed to a process for providing methanol to an MTO reactor system. The process includes providing a methanol-containing stream and directing the methanol-containing stream to the MTO reactor system. In this embodiment, the methanol-containing stream does not pass specification for Grade AA methanol.

In one embodiment, the present invention is a process for forming light olefins. The process includes the steps of: (a) providing a feedstock comprising liquid methanol and a contaminant selected from the group consisting of $SO_x$, carbonic acid, and $C_5$-hydrocarbons; (b) vaporizing at least a portion of the feedstock to form a vaporized feed stream, wherein the vaporized feed stream comprises vaporized methanol and at least a portion of the contaminant that was present in the feedstock; and (c) contacting the vaporized methanol with a catalyst in a reactor under conditions effective to convert at least a portion of the vaporized methanol to the light olefins. Optionally, the at least a portion of the contaminant comprises at least 0.001 weight percent, more preferably at least 0.01 weight percent, and most preferably at least 0.5 weight percent of the vaporized feed stream.

In another embodiment, the process of the present invention includes the steps of: (a) providing a feedstock comprising liquid methanol and a contaminant selected from the group consisting of soot and rust; (b) vaporizing at least a portion of the feedstock to form a vaporized feed stream and a blowdown stream, wherein the vaporized feed stream comprises vaporized methanol, and wherein the blowdown stream comprises at least a portion of the contaminant that was present in the feedstock; and (c) contacting the vaporized methanol with a catalyst in a reactor under conditions effective to convert at least a portion of the vaporized methanol to the light olefins.

In another embodiment, the inventive process includes the step of providing a methanol-containing stream comprising liquid methanol and solid contaminants, wherein the methanol-containing stream does not pass specification for Grade AA methanol. The methanol-containing stream is heated under conditions effective to form a vaporized feed stream and a liquid blowdown stream, wherein the vaporized feed stream comprises vaporized methanol, and the liquid blowdown stream comprises the solid contaminants. The vaporized methanol contacts a catalyst under conditions effective to convert at least a portion of the vaporized methanol to light olefins.

Having now fully described the invention, it will be appreciated by those skilled in the art that the invention may be performed within a wide range of parameters within what is claimed, without departing from the spirit and scope of the invention.

The invention claimed is:

1. A process for forming light olefins, the process comprising the steps of:
    (a) providing a methanol feedstock from a tanker which previously carried a non-methanol material or which was designed to carry a non-methanol material and which comprises a blanketing system for delivering medium to one or more holds, wherein the methanol has at least one contaminant selected from the group consisting of: soot, rust, leachable metals, $SO_x$, carbonic acid, and $C_5$-hydrocarbons;
    (b) vaporizing at least a portion of the feedstock to form a vaporized feed stream, wherein the vaporized feed stream comprises vaporized methanol and at least a portion of the contaminant that was present in the feedstock; and
    (c) contacting the vaporized methanol with a catalyst in a reactor under conditions effective to convert at least a portion of the vaporized methanol to tile light olefins.

2. The process of claim 1, wherein the at least a portion of the contaminant comprises at least 0.001 weight percent of the vaporized feed stream, based on the total weight of the vaporized feed stream.

3. The process of claim 2, wherein the at least a portion of the contaminant comprises at least 0.01 weight percent of the vaporized feed stream, based on the total weight of the vaporized feed stream.

4. The process of claim 3, wherein the at least a portion of the contaminant comprises at least 0.05 weight percent of the vaporized feed stream, based on the total weight of the vaporized feed stream.

5. The process of claim 1, wherein the contaminant is carbonic acid.

6. The process of claim 5, wherein the feedstock does not pass test ASTM D-1363 at 30 minutes and 68° F. for Grade A methanol.

7. The process of claim 1, wherein the contaminant is $SO_x$.

8. The process of claim 7, wherein the feedstock does not pass test ASTM D-3961 for Grade A methanol.

9. The process of claim 1, wherein the contaminant is $C_5$-hydrocarbons.

10. The process of claim 9, wherein the feedstock does not pass test ASTM D-1722 for Grade A methanol.

11. The process of claim 1, wherein the feedstock does not pass test ASTM D1209 for Grade A methanol.

12. The process of claim 1, wherein the feedstock does not pass test ASTM D-1363 at 30 minutes and 68° F. for Grade A methanol.

13. The process of claim 1, wherein the feedstock does not pass test ASTM D-1722 for Grade A methanol.

14. The process of claim 1, wherein the feedstock does not pass the clarity test for Grade A methanol.

15. The process of claim 1, wherein the feedstock does not pass ASTM E-346 for Grade A methanol.

16. The process of claim 1, wherein the feedstock does not pass ASTM D-1613 for Grade A methanol.

17. The process of claim 1, wherein the feedstock does not pass ASTM D-3961 for Grade A methanol.

18. The process of claim 1, wherein the non-methanol material comprises crude oil.

19. The process of claim 1, wherein the non-methanol material comprises naphtha.

20. The process of claim 1, wherein the blanketing medium comprises exhaust from a fuel burning engine.

21. The process of claim 20, wherein the blanketing medium comprises exhaust from a diesel burning engine.

22. The process of claim 20, wherein the blanketing medium comprises exhaust from a kerosene burning engine.

23. The process of claim 20, wherein the blanketing medium comprises exhaust from a methanol burning engine.

24. The process of claim 1, wherein the blanketing medium comprises nitrogen.

25. The process of claim 1, wherein the blanketing medium comprises carbon dioxide.

26. The process of claim 1, wherein the non-methanol material comprises crude oil.

27. The process of claim 1, wherein the non-methanol material comprises naphtha.

28. A process for forming light olefins, the process comprising the steps of:
 (a) providing a methanol feedstock from a tanker which previously carried a non-methanol material or which was designed to carry a non-methanol material and which comprises a blanketing system for delivering medium to one or more holds, wherein the methanol has at least one contaminant selected from the group consisting of soot and rust;
 (b) vaporizing at least a portion of the feedstock to form a vaporized feed stream and a blowdown stream, wherein the vaporized feed stream comprises vaporized methanol, and wherein the blowdown stream comprises at least a portion of the contaminant that was present in the feedstock; and
 (c) contacting the vaporized methanol with a catalyst in a reactor under conditions effective to convert at least a portion of the vaporized methanol to the light olefins.

29. The process of claim 28, wherein the contaminant is soot.

30. The process of claim 29, wherein the feedstock does not pass test ASTM D-1209 for Grade A methanol.

31. The process of claim 28, wherein the contaminant is rust.

32. The process of claim 31, wherein the feedstock does not pass test ASTM D-1363 at 30 minutes and 68° F. for Grade A methanol.

33. The process of claim 31, wherein the feedstock does not pass test ASTM D-1613 for Grade A methanol.

34. The process of claim 31, wherein the feedstock does not pass test ASTM E-346 for Grade A methanol.

35. The process of claim 28, wherein the feedstock does not pass test ASTM D-1363 at 30 minutes and 68° F. for Grade A methanol.

36. The process of claim 28, wherein the feedstock does not pass test ASTM D-1722 for Grade A methanol.

37. The process of claim 28, wherein the feedstock does not pass the clarity test for Grade A methanol.

38. The process of claim 28, wherein the feedstock does not pass ASTM E-346 for Grade A methanol.

39. The process of claim 28, wherein the feedstock does not pass ASTM D-1613 for Grade A methanol.

40. The process of claim 28, wherein the feedstock does not pass ASTM D-3961 for Grade A methanol.

41. The process of claim 28, wherein the non-methanol material comprises crude oil.

42. The process of claim 28, wherein the non-methanol material comprises naphtha.

43. The process of claim 28, wherein the blanketing medium comprises exhaust from a fuel burning engine.

44. The process of claim 43, wherein the blanketing medium comprises exhaust from a diesel burning engine.

45. The process of claim 43, wherein the blanketing medium comprises exhaust from a kerosene burning engine.

46. The process of claim 43, wherein the blanketing medium comprises exhaust from a methanol burning engine.

47. The process of claim 28, wherein the blanketing medium comprises nitrogen.

48. The process of claim 28, wherein the blanketing medium comprises carbon dioxide.

49. The process of claim 28, wherein the non-methanol material comprises crude oil.

50. The process of claim 28, wherein the non-methanol material comprises naphtha.

* * * * *